(12) United States Patent
Deuel et al.

(10) Patent No.: US 11,696,753 B2
(45) Date of Patent: Jul. 11, 2023

(54) SUTURE CINCHING DEVICE WITH CUTTER

(71) Applicant: BOSTON SCIENTIFIC SCIMED, INC., Maple Grove, MN (US)

(72) Inventors: Christopher R. Deuel, Melrose, MA (US); Ryan V. Wales, Northborough, MA (US); Sean P. Fleury, Minneapolis, MN (US); Stan Robert Gilbert, Litchfield, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 337 days.

(21) Appl. No.: 17/089,641

(22) Filed: Nov. 4, 2020

(65) Prior Publication Data
US 2021/0128141 A1 May 6, 2021

Related U.S. Application Data

(60) Provisional application No. 62/930,786, filed on Nov. 5, 2019.

(51) Int. Cl.
*A61B 17/04* (2006.01)
*A61B 17/00* (2006.01)

(52) U.S. Cl.
CPC ............. *A61B 17/0467* (2013.01); *A61B 2017/00477* (2013.01); *A61B 2017/0496* (2013.01)

(58) Field of Classification Search
CPC ...... A61B 17/0467; A61B 2017/00477; A61B 2017/0496
See application file for complete search history.

(56) References Cited

U.S. PATENT DOCUMENTS

| 7,094,246 | B2 * | 8/2006 | Anderson | A61B 17/0467 606/139 |
| 7,879,055 | B1 * | 2/2011 | Stone | A61B 17/0467 606/170 |
| 7,993,368 | B2 | 8/2011 | Gambale et al. | |
| 8,211,123 | B2 * | 7/2012 | Gross | A61B 17/0469 606/167 |
| 8,282,659 | B2 * | 10/2012 | Oren | A61B 17/0467 606/139 |
| 8,444,673 | B2 | 5/2013 | Thielen et al. | |
| 8,540,735 | B2 | 9/2013 | Mitelberg et al. | |

(Continued)

FOREIGN PATENT DOCUMENTS

WO    2019226891 A1    11/2019

OTHER PUBLICATIONS

Invitation to Pay Additional Fees dated Jan. 14, 2021 for International Application No. PCT/US2020/058976.

(Continued)

*Primary Examiner* — Ryan J. Severson
(74) *Attorney, Agent, or Firm* — Seager, Tufte & Wickhem LLP

(57) ABSTRACT

Medical devices for cinch and cutting one or more suture, and methods for making and using such devices are disclosed. An example medical device may include a coupler, a sleeve releasably coupled to the coupler, a cutter slidably disposed within the sleeve, and a suture cinching member movable into and out of the sleeve. A wire may extend through and be longitudinally movable within the coupler to move the suture cinching member and cutter.

20 Claims, 17 Drawing Sheets

(56) References Cited

U.S. PATENT DOCUMENTS

| | | | |
|---|---|---|---|
| 8,834,497 B2* | 9/2014 | Snell | A61B 17/0467 606/167 |
| 8,911,457 B2* | 12/2014 | Koogle, Jr. | A61B 17/0469 606/148 |
| 8,911,461 B2* | 12/2014 | Traynor | A61B 17/0467 606/139 |
| 8,974,371 B2 | 3/2015 | Durgin et al. | |
| 9,247,935 B2* | 2/2016 | George | A61B 17/0467 |
| 9,332,980 B2* | 5/2016 | George | A61B 17/0467 |
| 9,486,192 B2 | 11/2016 | Pipenhagen | |
| 9,642,615 B2* | 5/2017 | Halac | A61B 17/0467 |
| 9,788,831 B2 | 10/2017 | Mitelberg | |
| 10,143,464 B2* | 12/2018 | George | A61B 17/0469 |
| 10,426,457 B2 | 10/2019 | Mitelberg et al. | |
| 10,426,462 B2* | 10/2019 | Haberman | A61B 17/0467 |
| 11,219,447 B2* | 1/2022 | Juan | A61B 17/06166 |
| 2003/0120287 A1* | 6/2003 | Gross | A61B 17/0469 606/148 |
| 2004/0097865 A1* | 5/2004 | Anderson | A61B 17/0467 604/22 |
| 2007/0173865 A1* | 7/2007 | Oren | A61B 17/0467 606/148 |
| 2008/0228198 A1* | 9/2008 | Traynor | A61B 17/0467 606/138 |
| 2009/0228026 A1* | 9/2009 | Koogle, Jr. | A61B 17/0467 606/148 |
| 2011/0196388 A1 | 8/2011 | Thielen et al. | |
| 2012/0136378 A1* | 5/2012 | Snell | A61B 17/0467 606/148 |
| 2012/0158023 A1 | 6/2012 | Mitelberg et al. | |
| 2012/0259346 A1 | 10/2012 | Hansen et al. | |
| 2013/0072949 A1* | 3/2013 | Halac | A61B 17/0487 606/148 |
| 2014/0277123 A1* | 9/2014 | Mitelberg | A61B 17/0469 606/228 |
| 2015/0088163 A1* | 3/2015 | George | A61B 17/0469 606/138 |
| 2015/0142022 A1* | 5/2015 | George | A61B 17/0469 606/148 |
| 2016/0242765 A1* | 8/2016 | George | A61B 17/0467 |
| 2018/0028180 A1 | 2/2018 | Binmoeller et al. | |
| 2018/0228485 A1* | 8/2018 | Haberman | A61B 17/0469 |
| 2019/0357899 A1 | 11/2019 | Gilbert et al. | |
| 2019/0374215 A1* | 12/2019 | Juan | A61B 17/06166 |
| 2020/0178956 A1 | 6/2020 | Mitelberg et al. | |
| 2021/0128141 A1* | 5/2021 | Deuel | A61B 17/1227 |

OTHER PUBLICATIONS

International Search Report and Written Opinion dated Jan. 13, 2021 for International Application No. PCT/US2020/058975.

* cited by examiner

SUTURE CINCHING DEVICE WITH CUTTER

CROSS REFERENCE TO RELATED APPLICATIONS

The present application claims the benefit of and priority to U.S. Provisional Patent Application Ser. No. 62/930,786, filed on Nov. 5, 2019, titled SUTURE CINCHING DEVICE WITH CUTTER, the disclosure of which is incorporated herein by reference.

TECHNICAL FIELD

The present disclosure pertains to medical devices, and methods for manufacturing medical devices. More particularly, the present disclosure pertains to devices for cinching and cutting a suture, and methods for manufacturing and using such devices.

BACKGROUND

A wide variety of medical devices and methods have been developed for suturing tissue, and securing and/or terminating the free end of a suture relative to the tissue once a suture is in place. These devices are manufactured by any one of a variety of different manufacturing methods and may be used according to any one of a variety of methods. Of the known devices and methods, each has certain advantages and disadvantages. There is an ongoing need to provide alternative devices as well as alternative methods for manufacturing and using such devices.

SUMMARY

This disclosure provides design, material, manufacturing method, and use alternatives for suture termination devices, for example, devices for applying a cinch to a suture. In an example, a medical device for cinching and cutting one or more suture comprises a coupler having a coupler lumen, a sleeve releasably coupled to the coupler, the sleeve having a sidewall defining a sleeve lumen, the sidewall having a window into the sleeve lumen, a cutter slidably disposed within the sleeve, the cutter having a cutting surface, a suture cinching member moveable into and out of the sleeve lumen, and a wire extending through and longitudinally movable within at least the coupler, the wire releasably connected to the cutter.

Alternatively or additionally to any of the above examples, when the wire is in a distal position, the suture cinching member is in a first configuration for receiving one or more suture, and proximal movement of the wire pulls the suture cinching member at least partially into the sleeve into a second configuration in which a portion of the one or more suture is cinched within the sleeve and cut by the cutting surface of the cutter.

Alternatively or additionally to any of the above examples, the cutter is configured such that when the suture cinching member is in the second configuration, further proximal movement of the wire causes the wire to be released from the cutter and the coupler to be released from the sleeve.

Alternatively or additionally to any of the above examples, the cutter comprises a cutting member and a cutter actuator, the cutting member defining a cutter lumen with an opening extending into the cutter lumen, the opening defining the cutting surface, wherein the cutter actuator includes a distal rod connected to the suture cinching member.

Alternatively or additionally to any of the above examples, the cutter actuator is connected to the suture cinching member and the wire, such that movement of the wire results in movement of the suture cinching member and the cutting member.

Alternatively or additionally to any of the above examples, the suture cinching member includes a proximal portion configured to fit within the sleeve lumen, wherein when the suture cinching member is in the first configuration, the suture cinching member is positioned such that the proximal portion is spaced apart from an inner surface of the sleeve and the cutter is positioned with the opening aligned with the window in the sleeve.

Alternatively or additionally to any of the above examples, when in the suture cinching member is moved to the second configuration, the suture cinching member and attached cutter are moved proximally until the proximal portion of the suture cinching member engages the inner surface of the sleeve and the opening in the cutter is proximal of the window in the sleeve.

Alternatively or additionally to any of the above examples, the suture cinching member has a distal head with an outer diameter greater than a diameter of the sleeve lumen, wherein in the second configuration the distal head abuts a distal end of the sleeve.

Alternatively or additionally to any of the above examples, the coupler has a projection extending into the coupler lumen, the cutter includes a proximal coupling member, and the wire includes a distal end removably coupled to the proximal coupling member of the cutter, wherein when the suture cinching member is in the second configuration, further proximal movement of the wire causes the proximal coupling member to engage the projection, stopping its proximal movement and releasing the distal end of the wire, and releasing the coupler from the sleeve.

Alternatively or additionally to any of the above examples, the sleeve has an opening through the sidewall proximal of the window, and the cutter further comprises at least one deflectable wing configured to move into the opening when the suture cinching member moves into the second configuration.

Alternatively or additionally to any of the above examples, the cutter is coupled to a yoke and the yoke is removably coupled to the wire, wherein the suture cinching member includes first and second opposing clamp arms fixed to the yoke.

Alternatively or additionally to any of the above examples, the yoke is axially moveable within the sleeve lumen between a first position in which distal ends of the first and second opposing clamp arms are spaced apart, and a second position in which the distal ends are in contact with one another.

Alternatively or additionally to any of the above examples, the first and second opposing clamp arms are biased in the first position such that when at least distal portions of the first and second opposing clamp arms are disposed distal of the sleeve, the first and second opposing clamp arms are in the first position, and moving the first and second opposing clamp arms proximally into the sleeve moves the first and second opposing clamp arms into the second position.

Alternatively or additionally to any of the above examples, the cutter is disposed between the first and second opposing clamp arms.

Alternatively or additionally to any of the above examples, the cutting surface is a linear cutting surface disposed transverse to a longitudinal axis of the sleeve.

Alternatively or additionally to any of the above examples, a distal end of the first clamp arm has a rounded concave surface and a distal end of the second clamp arm has a rounded convex surface configured to engage the rounded concave surface on the first clamp arm.

Alternatively or additionally to any of the above examples, when the first and second opposing clamp arms are in the second position, one or more suture disposed between the first and second opposing clamp arms is clamped at a first location between the distal ends of the first and second opposing clamp arms and at a second location distal of the cutter.

Alternatively or additionally to any of the above examples, the cutter is configured such that when the first and second opposing clamp arms are moved from the first position to the second position over one or more suture, the first and second opposing clamp arms clamp the one or more suture and the cutting surface cuts the one or more suture.

In another example, a medical device for applying a cinch to one or more suture comprises an elongate shaft defining a shaft lumen, a sleeve having a sleeve lumen and a window extending into the sleeve lumen, first and second opposing clamp arms fixed to a yoke, wherein the yoke is axially moveable within the sleeve lumen between a first position in which distal ends of the first and second opposing clamp arms are spaced apart, and a second position in which the distal ends are in contact with one another, a cutter coupled to the first and second opposing clamp arms, the cutter defining a cutting surface, the cutter configured such that when the first and second opposing clamp arms are moved from the first position to the second position over one or more suture, the first and second opposing clamp arms clamp the one or more suture and the cutting surface cuts the one or more suture.

In a further example, a method of cinching and cutting one or more suture comprises engaging one or more suture with a suture cinching member, a distal portion of the suture cinching member disposed distal of a sleeve and a proximal portion of the suture cinching member disposed within a lumen of the sleeve, the suture cinching member connected to a cutter slidably disposed within the sleeve lumen, and moving the suture cinching member and connected cutter proximally into the sleeve, thereby engaging a cutting surface on the cutter with the one or more suture and cutting the one or more suture.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
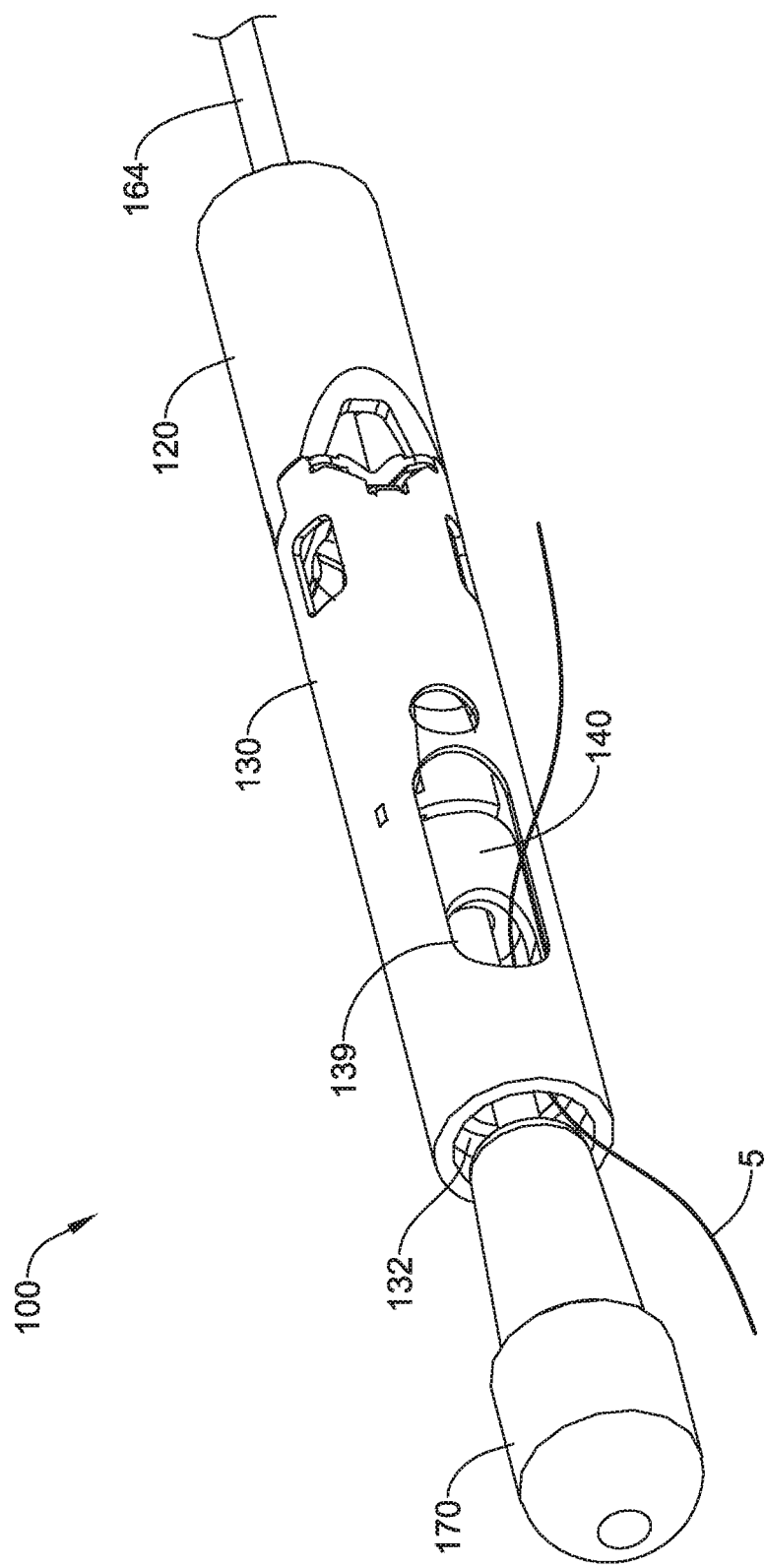
FIG. 1 is a perspective view of a portion of an example medical device for cinching and cutting a suture.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Medical suturing is used in a number of different interventions. Some of the interventions may include endoscopic suturing at remote sites within the patient and/or otherwise at sites that may be challenging to access. When the suturing process is complete, it may be desirable to terminate the suture in a way that maintains the suture so that the suture does not easily come undone. This may include using a device such as a cinch in order to maintain the suture. Disclosed herein are medical devices that may be used to secure and cut the suture. The medical devices disclosed herein may be delivered through the working channel of an endoscope. At least some of these devices utilize a cinch to maintain the suture. Some example remote sites in which the medical devices disclosed herein may be utilized include, without limitation, the gastro-intestinal (GI) tract, including the stomach, esophagus, and intestines, and within the heart including the heart valves and chambers. Some example procedures in which the devices may be used include, without limitation, gastric bypass, closure of perforations, full thickness resections, closure of post endoscopic submucosal dissection (ESD) sites, gastro jejunal anastomosis and lower esophageal sphincter (LES) repair, stent fixation, bariatric revision and closure of defects, and heart valve repair and replacement. Some additional details of such devices are disclosed herein.

FIGS. 1-6 illustrate an example medical device 100 configured to secure and cut a suture. This embodiment may include a suture cinching member such as cinch lock 170, a sleeve 130, a cutter assembly 140, a coupler 120, and wire 164. As shown in FIG. 1, a suture 5 may be threaded into the distal end 132 of the sleeve 130, through a portion of the cutter assembly 140, and out through a window 139 of the sleeve 130.

Figure 2:
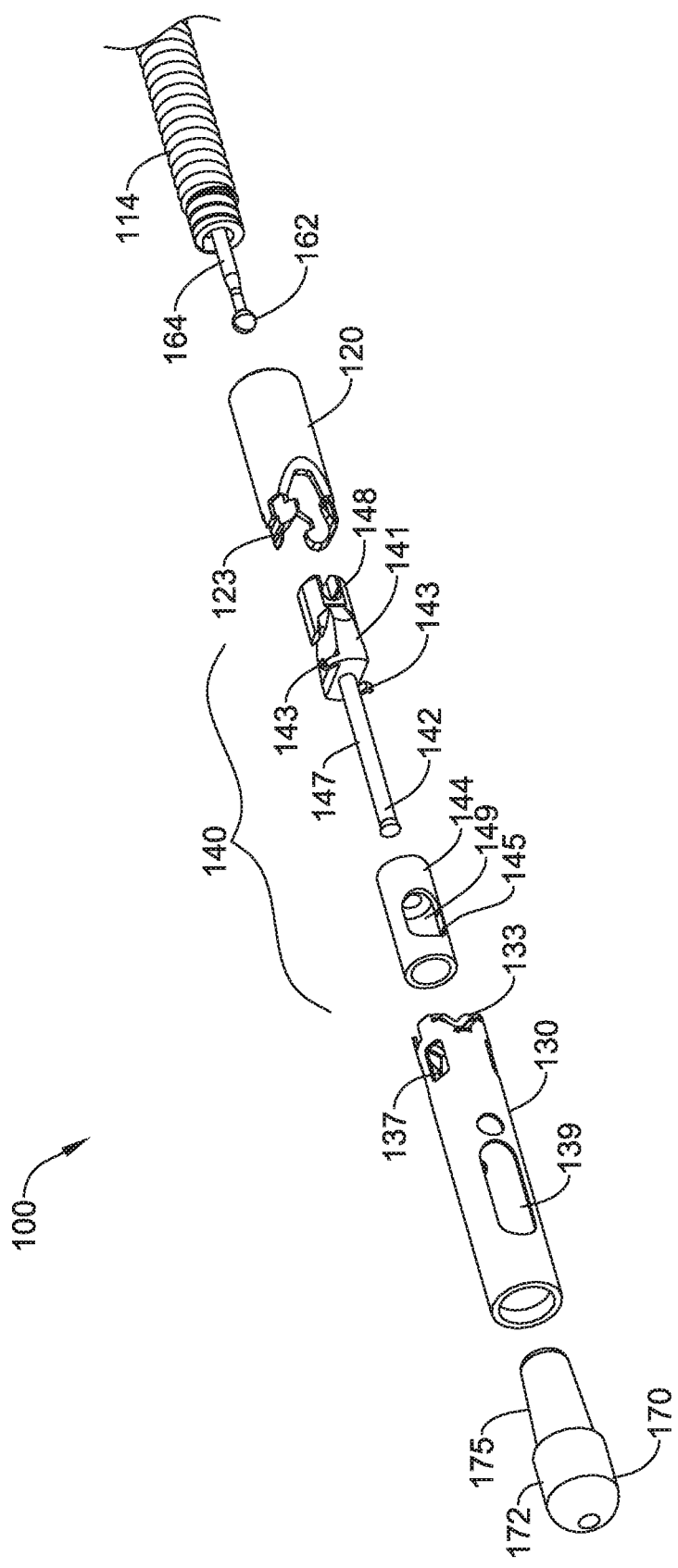
FIG. 2 is an exploded perspective view of the medical device as shown in FIG. 1.
Figure 3:
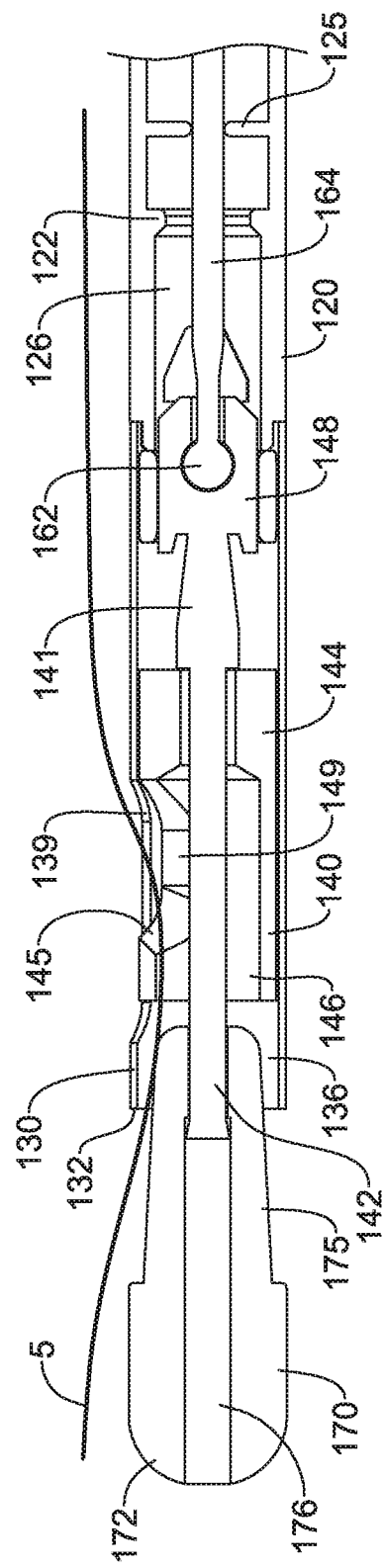
FIG. 3 is a cross-sectional view of the medical device as shown in FIG. 1, in a first configuration.

The exploded perspective view in FIG. 2 shows the separate elements of the medical device 100, and the cross-sectional view in FIG. 3 shows the internal structure of the assembled medical device 100 in a first configuration. While not illustrated in FIGS. 1 and 3-6, the medical device 100 may include an elongated shaft 114 attached to the coupler 120, as shown in FIG. 2, similar to the elongated shaft 214 discussed below. The cinch lock 170 may have a distal head 172, a proximal portion 175, and a lumen 176 extending at least part way through the distal head 172. The distal head 172 may have an outer diameter greater than or equal to the diameter of the sleeve lumen 136, while the proximal portion 175 is sized and configured to be received within the sleeve lumen 136 in a friction fit. The sleeve 130 may have a sidewall defining a sleeve lumen 136, a window 139 and at least one opening 137 extending through the sidewall. The opening 137 may be disposed proximal of the window 139. The sleeve 130 may further include a proximal connector 133.

The cutter assembly 140 may include a cutting member 144 disposed over a cutter actuator 147. The cutting member 144 may have a lumen 146 with an opening 149 extending into the lumen 146, where the opening 149 defines a cutting surface 145. The cutter actuator 147 may include a cutter connector 141 and a distal rod 142 configured to extend through the lumen 146 in the cutting member 144 and fit within the lumen 176 of the cinch lock 170 with an interference fit. The cutter actuator 147 may have a proximal coupling member 148 configured to releasably receive an enlarged distal end 162 of the wire 164. The cutter actuator 147 may further include at least one deflectable wing 143 configured to extend into the opening 137 in the sleeve 130 and lock the cutter assembly 140 to the sleeve 130. In the example shown in FIG. 2, the cutter actuator 147 includes a pair of opposing deflectable wings 143 and the sleeve 130 includes a pair of opposing openings 137.

The coupler 120 may define a coupler lumen 126 configured to receive the wire 164, and a distal connector 123 configured to releasably connect with the proximal connector 133 on the sleeve 130. The coupler 120 may include a protrusion 122 extending into the coupler lumen 126. The protrusion 122 may provide a stop for the proximal coupling member 148, preventing further proximal movement of the proximal coupling member 148 through the coupler 120. The coupler 120 may also have an engagement member 125 disposed within the coupler lumen 126, the engagement member 125 configured to prevent the enlarged distal end 162 of the wire 164 from passing proximally through the coupler 120.

The medical device 100 functions to secure or cinch and then cut a suture. When the cutter assembly 140 and cinch lock 170 are in a first, open configuration, as shown in FIG. 3, a suture 5 may be threaded into the distal end 132 of the sleeve 130 and between the proximal portion 175 of the cinch lock 170 and the inner surface of the sleeve lumen 136, then through the lumen 146 of the cutting member 144 and out the opening 149 of the cutting member 144 and the window 139 of the sleeve 130.

Figure 4:
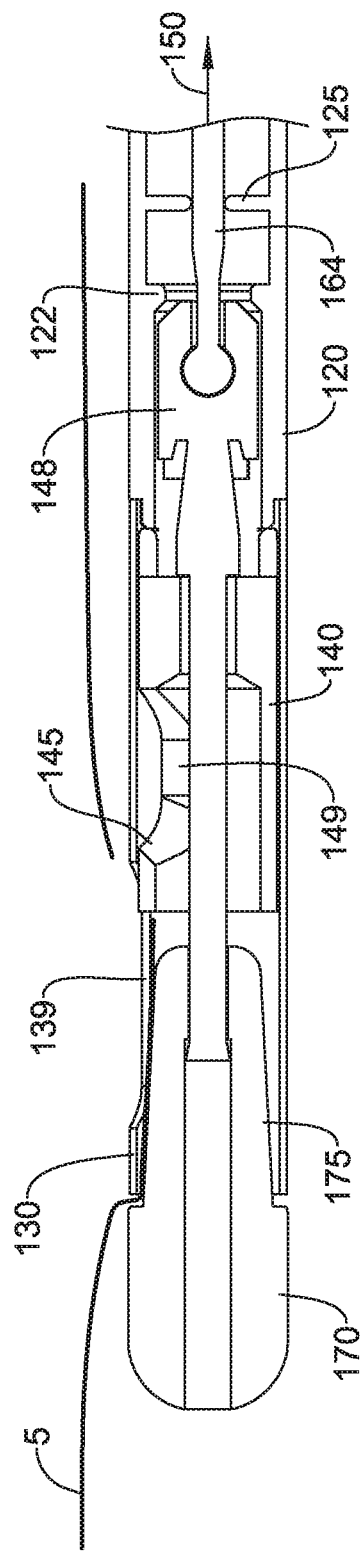
FIG. 4 a cross-sectional view of the medical device as shown in FIG. 1, in a second configuration.
Figure 5:
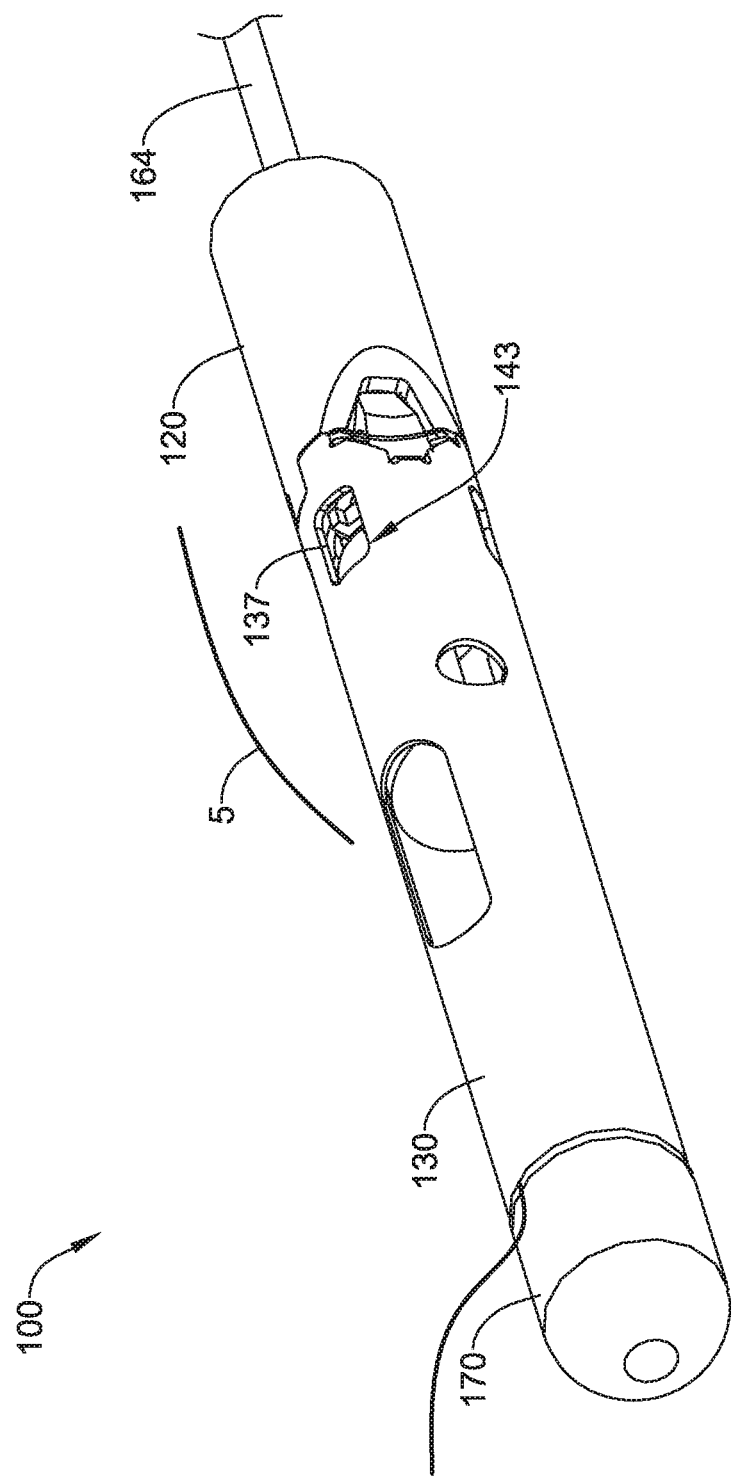
FIG. 5 is a perspective view of the medical device as shown in FIG. 1, in the second configuration.

FIGS. 4 and 5 show the suture 5 being secured and cut. From the first configuration shown in FIG. 3, the wire 164 is pulled proximally, indicated by arrow 150, which pulls the proximal portion 175 of the cinch lock 170 into the sleeve 130, thereby cinching and securing the suture. The cutter assembly 140 is also moved proximally, pinching and then cutting the suture 5 as the cutting surface 145 passes under the wall of the sleeve 130. As shown in FIG. 4, the suture 5 is secured between the proximal portion 175 and the inner surface of the sleeve lumen 136. The interference fit between the proximal portion 175 and the inner surface of the sleeve lumen 136 secures the suture 5 even when there is a gap between the proximally facing shoulder surface of the cinch lock 170 and the distal end 132 of the sleeve 130, as shown in FIGS. 4 and 5. This gap may prevent crimping and possible damage to the suture as it bends at an approximately right angle. However, in other examples, the cinch lock 170 may be pulled proximally until the proximally facing shoulder surface engages the distal end 132 of the sleeve 130, thereby providing an additional securement point. In such an example, the edges of the proximally facing shoulder surface and the distal end 132 of the sleeve 130 are generally smooth to prevent damage to the suture.

Figure 6:
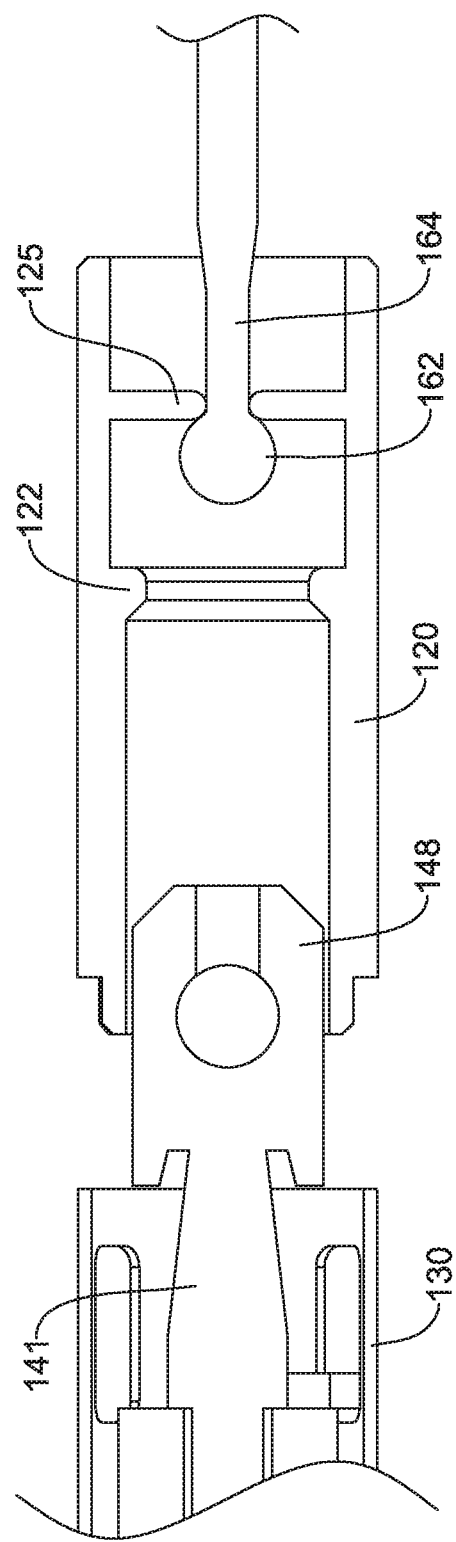
FIG. 6 is a cross-sectional view of a portion of the medical device as shown in FIG. 1, in a third configuration.

Further proximal movement of the wire 164 may cause the proximal coupling member 148 of the cutter connector 141 to contact the protrusion 122 of the coupler 120. Simultaneous to this, the deflectable wings 143 on the cutter connector 141 will pop into the openings 137 of the sleeve 130, as shown in FIG. 5, preventing the cutter assembly 140 from being pulled proximally or advanced distally out of the sleeve 130. Pulling the wire 164 proximally while the proximal coupling member 148 contacts the protrusion 122 uncouples the enlarged distal end 162 of the wire 164 from the proximal coupling member 148, as shown in FIG. 6. When the enlarged distal end 162 engages the engagement member 125 within the coupler 120, further proximal movement of the wire 164 uncouples the proximal connector 133 on the sleeve 130 from the distal connector 123 on the coupler 120. This allows the sleeve 130, cutter assembly 140, and cinch lock 170 to be uncoupled from the coupler 120 and wire 164, deploying them in to the lumen. The coupler 120 and wire 164 may then be removed from the body. This will keep the cinch in place and the suture tight for an extended period.

FIGS. 7-15B illustrate a further embodiment of suture cinching and cutting device 200. Many elements of this device 200 are similar to those of the tension member release clip described in U.S. Pat. No. 8,974,371, the entire disclosure of which is incorporated herein by reference.

Figure 7:
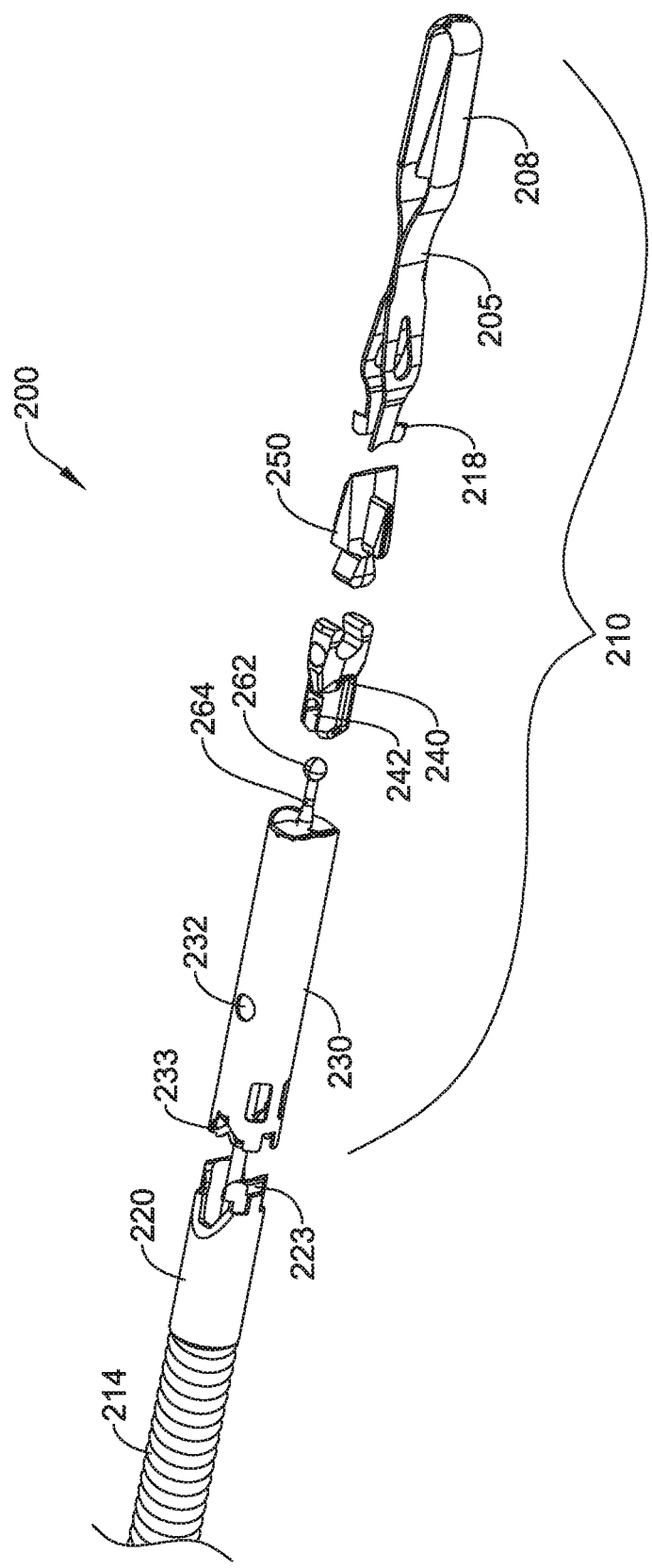
FIG. 7 is a perspective exploded view of a portion of another example medical device for cinching and cutting a suture.
Figure 8:
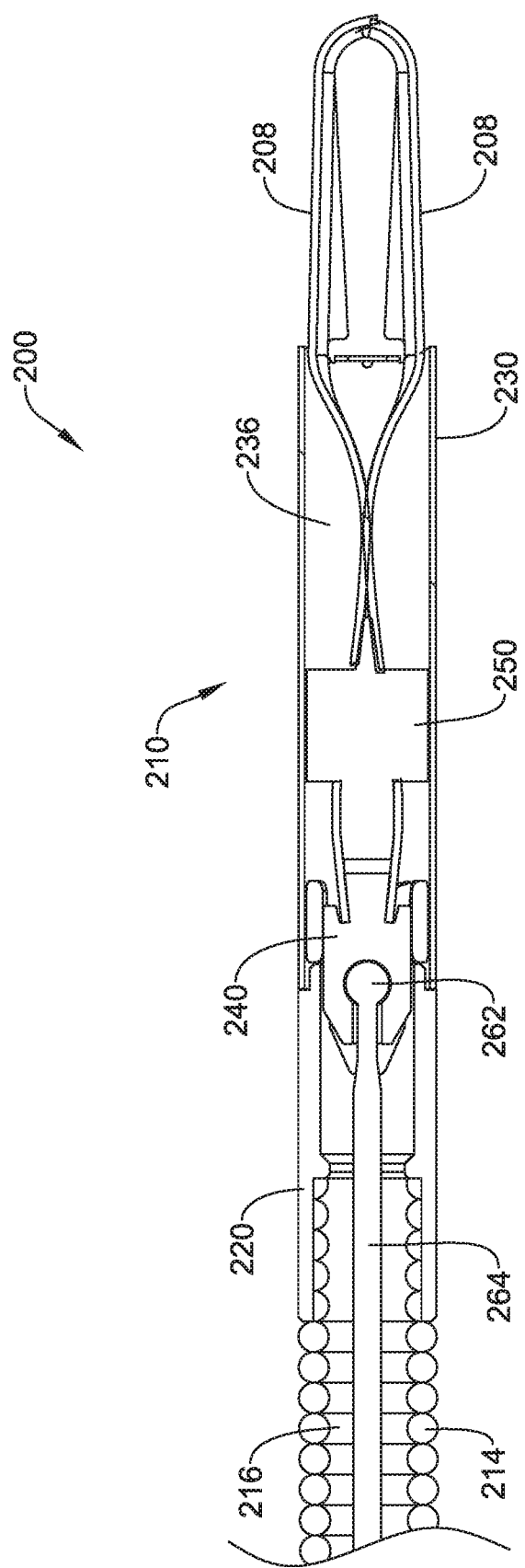
FIG. 8 is a top cross-sectional view of the medical device as shown in FIG. 7 in a closed configuration.

The exploded view in FIG. 7 shows the elements of the device 200, and FIG. 8 shows the internal structure of the device 200 assembled and in a closed configuration. The device 200 may include a shaft 214 with an attached coupler 220 and a control wire 264 extending therethrough, and a suture clamping assembly 210 releasably connected to the coupler 220. The suture clamping assembly 210 may include a sleeve 230, a yoke 240, a cutter 250, and a suture cinching member such as a pair of clamp arms 208. The coupler 220 may have a distal connector 223 configured to releasably connect with a proximal connector 233 on the sleeve 230. The sleeve 230 may have a sleeve lumen 236 and a window 232 extending into the lumen 236. The control wire 264 may have an enlarged distal end 262 configured to be releasably engaged in a recess 242 in the yoke 240. The yoke 240 may be coupled with the cutter 250, and the cutter 250 may be engaged with the clamp arms 208.

Figure 9:
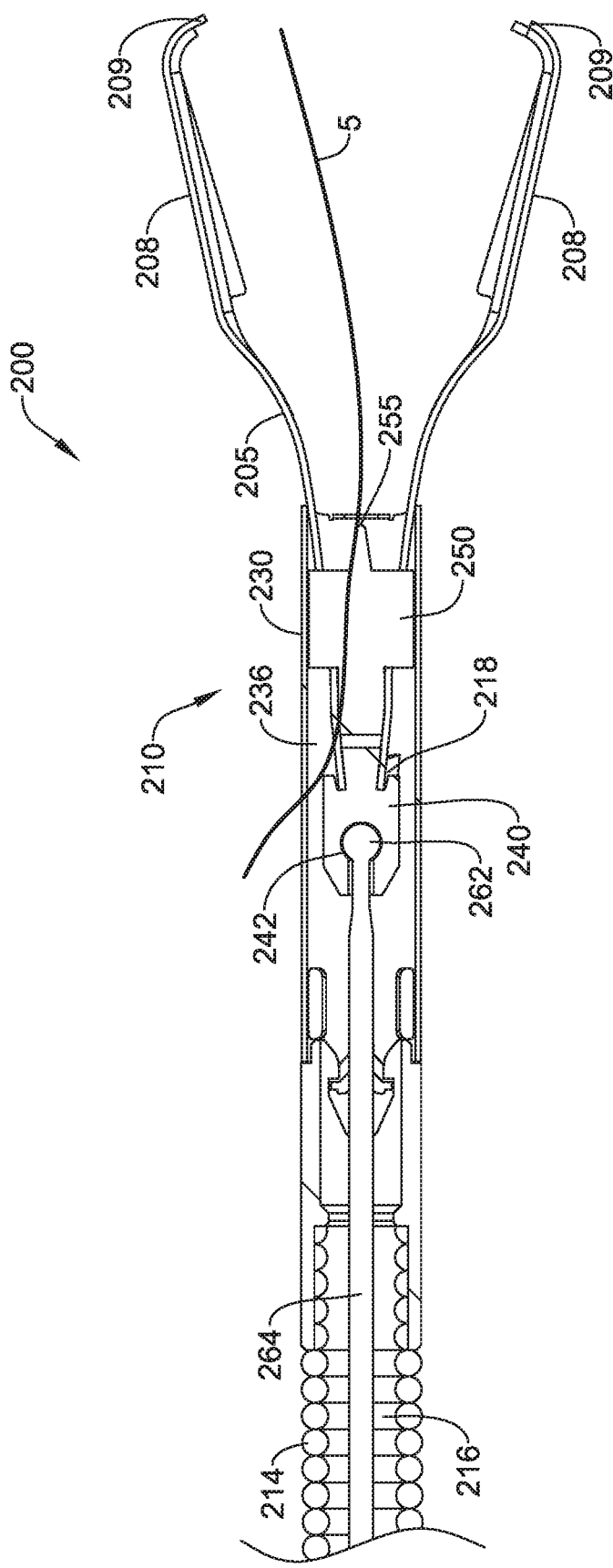
FIG. 9 is a top cross-sectional view of the medical device as shown in FIG. 7 in an open configuration.

FIG. 8 shows the device 200 with the suture clamping assembly 210 in the closed configuration for deployment. FIG. 9 shows the device 200 with the suture clamping assembly 210 in the open configuration. The suture clamping assembly 210 includes mechanisms slidably disposed within the sleeve lumen 236, converting proximal and distal movement of the control wire 264 into the actions necessary to open and close the suture clamping assembly 210. The clamp arms 208 move between a closed position, shown in FIG. 8, and an open position, shown in FIG. 9. The proximal ends 218 of the clamp arms 208 are fixed to the yoke 240. The cutter 250, including a cutting edge 255, is coupled between the clamp arms 208. The clamp arms 208 are biased in the open position by a spring section 205, as shown in FIG. 9, and revert to this open position whenever they are not constrained by the sleeve 230.

Figure 10:
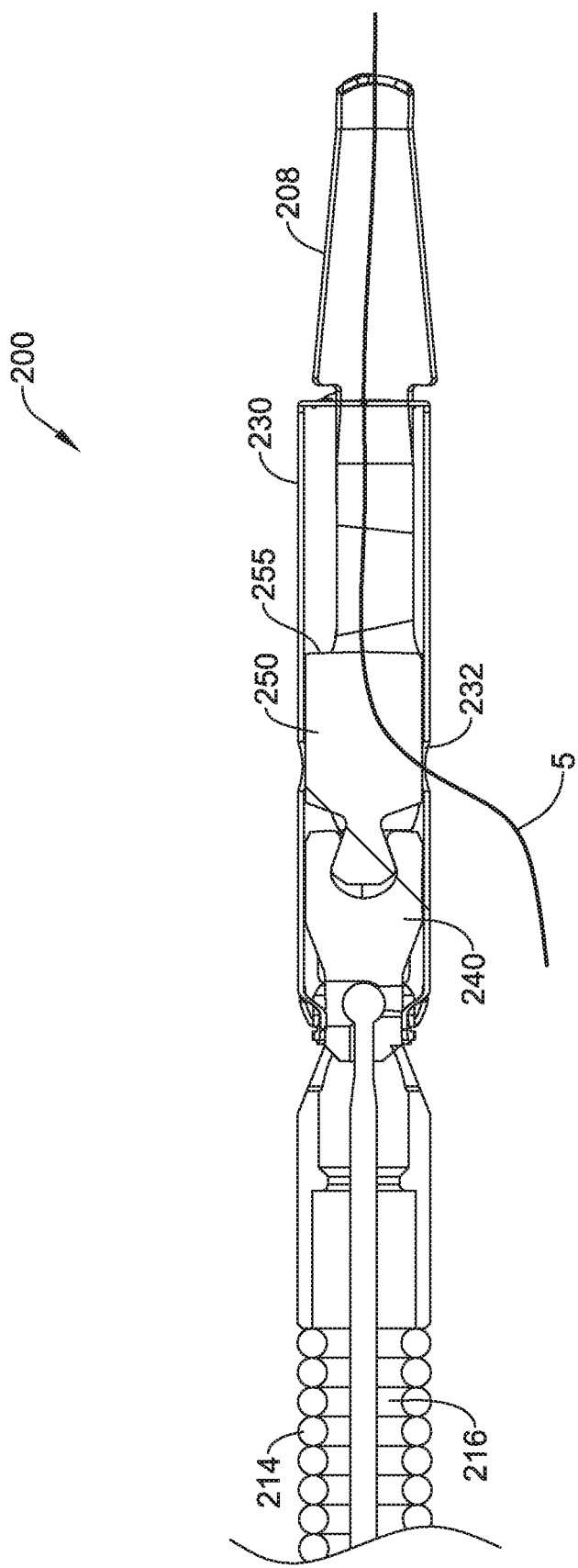
FIG. 10 is a side cross-sectional view of the medical device as shown in FIG. 7 in a closed configuration.

The suture clamping assembly 210 may be moved axially within the sleeve 230 by pushing or pulling the control wire 264 extending through the shaft lumen 216 and sleeve lumen 236. The suture clamping assembly 210 is in the closed position, shown in FIG. 8 for delivery. When the device 200 is at the target location, the control wire 264 may be pushed distally, moving the suture clamping assembly 210 toward the distal end of the sleeve 230. As the clamp arms 208 exit the sleeve 230, the clamp arms 208 separate, moving into the fully open position shown in FIG. 9. A suture 5 may then be placed between the clamp arms 208 and threaded into the sleeve 230 adjacent the cutter 250 and out the window 232. See FIG. 10. The control wire 264 may then be pulled proximally, moving the suture clamping assembly 210 proximally through the sleeve 230, bringing the clamp arms 208 together as they slide proximally within the sleeve 230 until the distal ends 209 of the clamp arms 208 come into contact with each other, clamping the suture 5 therebetween, as shown in FIG. 10.

Figure 11:
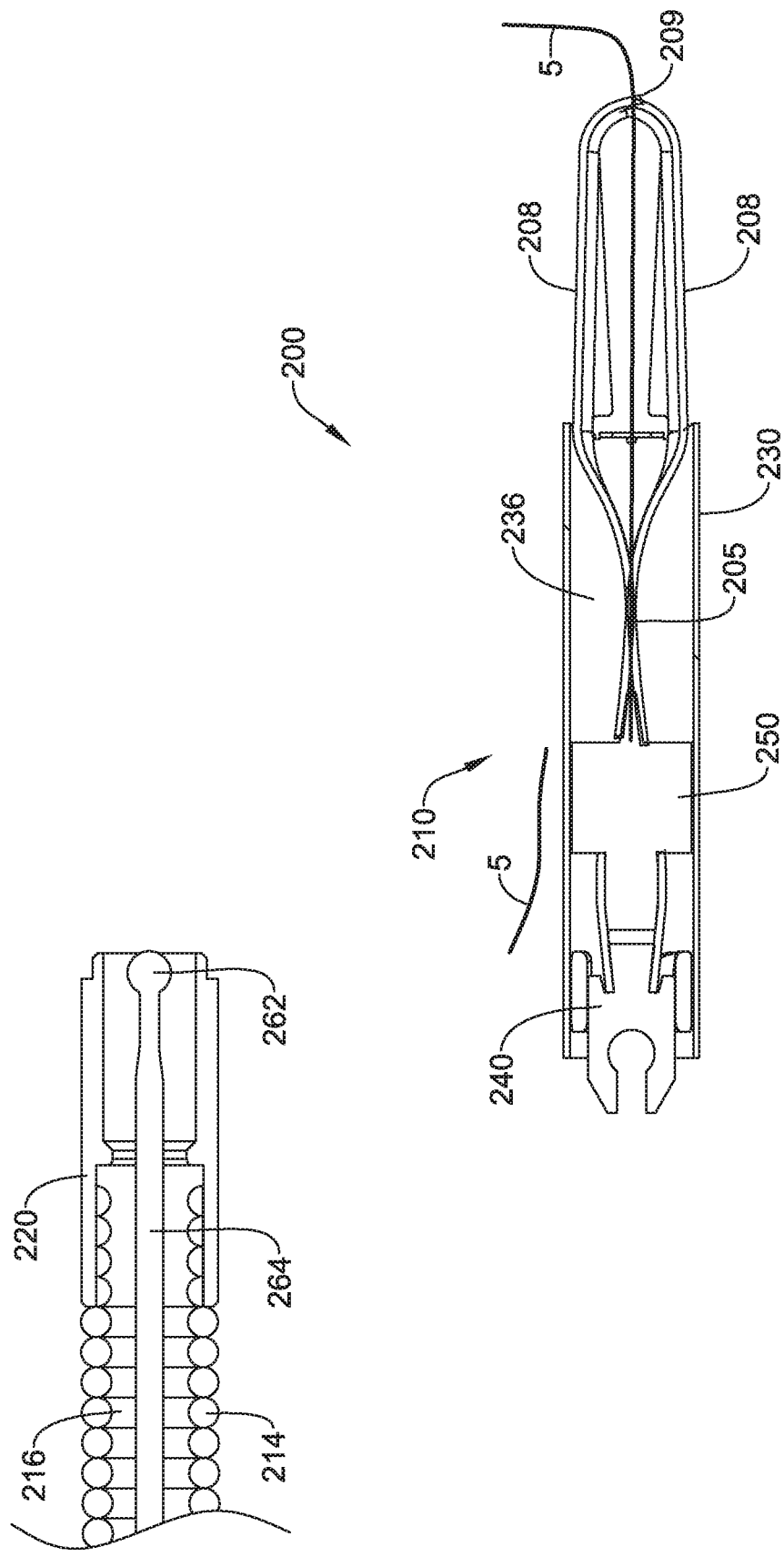
FIG. 11 is a top cross-sectional view of the medical device as shown in FIG. 7 in a closed and separated configuration.

As the suture clamping assembly 210 moves proximally within the sleeve 230 and the suture 5 is clamped between the clamp arms 208, the suture 5 engages the cutting edge 255 of the cutter 250 and is severed, as shown in FIG. 11. In the closed or clamped position, the suture 5 may be clamped between the clamp arms 208 at two locations: between the distal ends 209 and the spring section 205 distal of the cutter 250.

Figure 12:
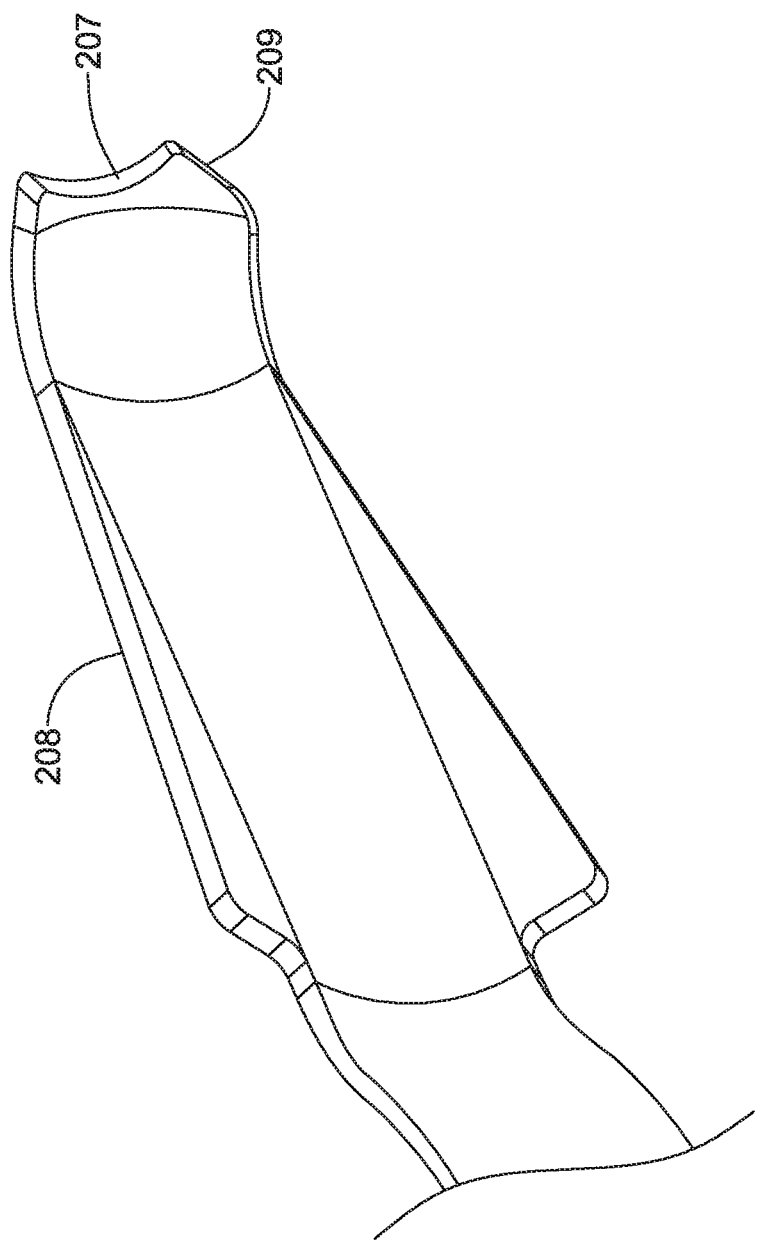
FIG. 12 is a close-up perspective view of the distal end of a clamp arm of the medical device as shown in FIG. 7.

FIG. 12 shows a close-up of the distal end 209 of the clamp arm 208, illustrating a rounded edge 207 that prevents cutting of the suture 5 when the suture 5 is firmly clamped between opposing clamp arms 208. In some examples, one clamp arm 208 may have a concave rounded edge 207 as shown in FIG. 12 and the other clamp arm 208 may have a matching convex rounded edge (not shown).

Figure 13:
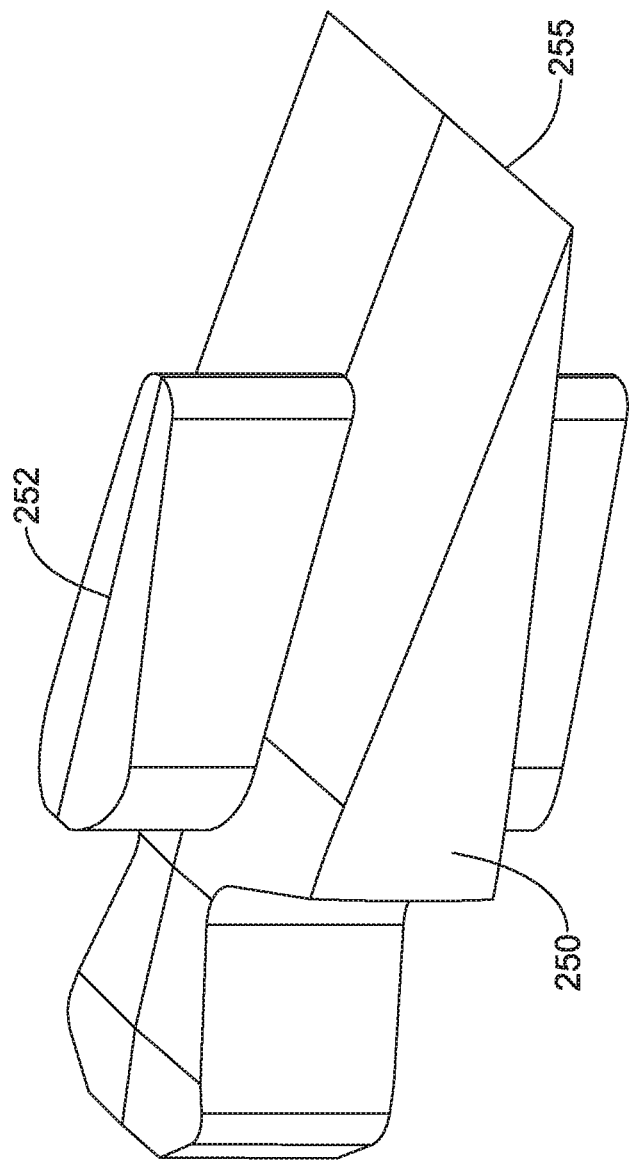
FIG. 13 is a perspective view of a cutter of the medical device as shown in FIG. 7.
Figure 14:
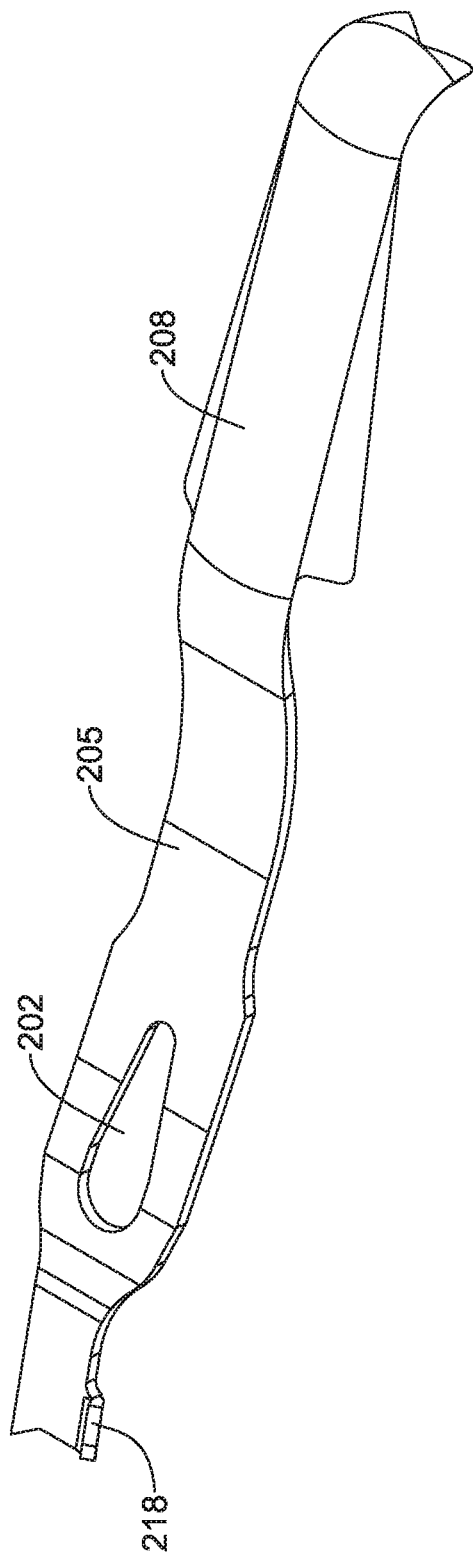
FIG. 14 is a perspective view of a clamp arm of the medical device as shown in FIG. 7.
Figure 15A:
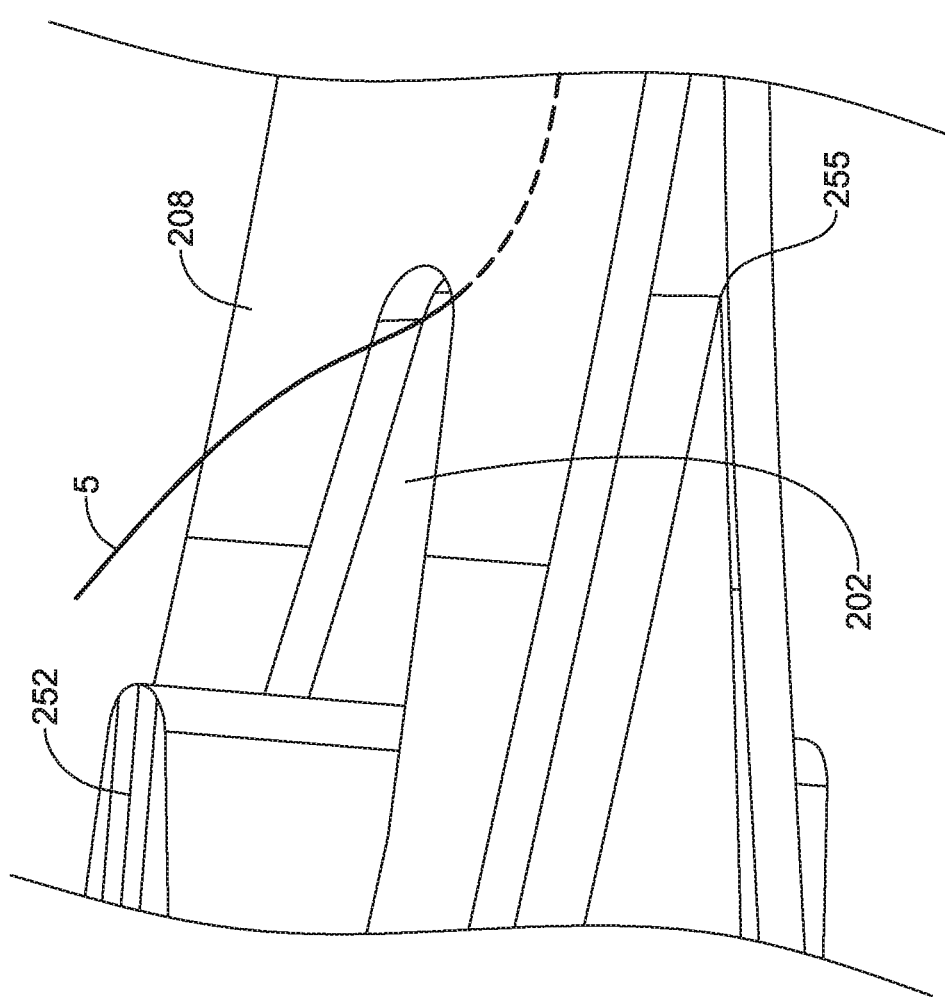
FIGS. 15A and 15B are perspective views of a portion of the medical device as shown in FIG. 7.
Figure 15B:
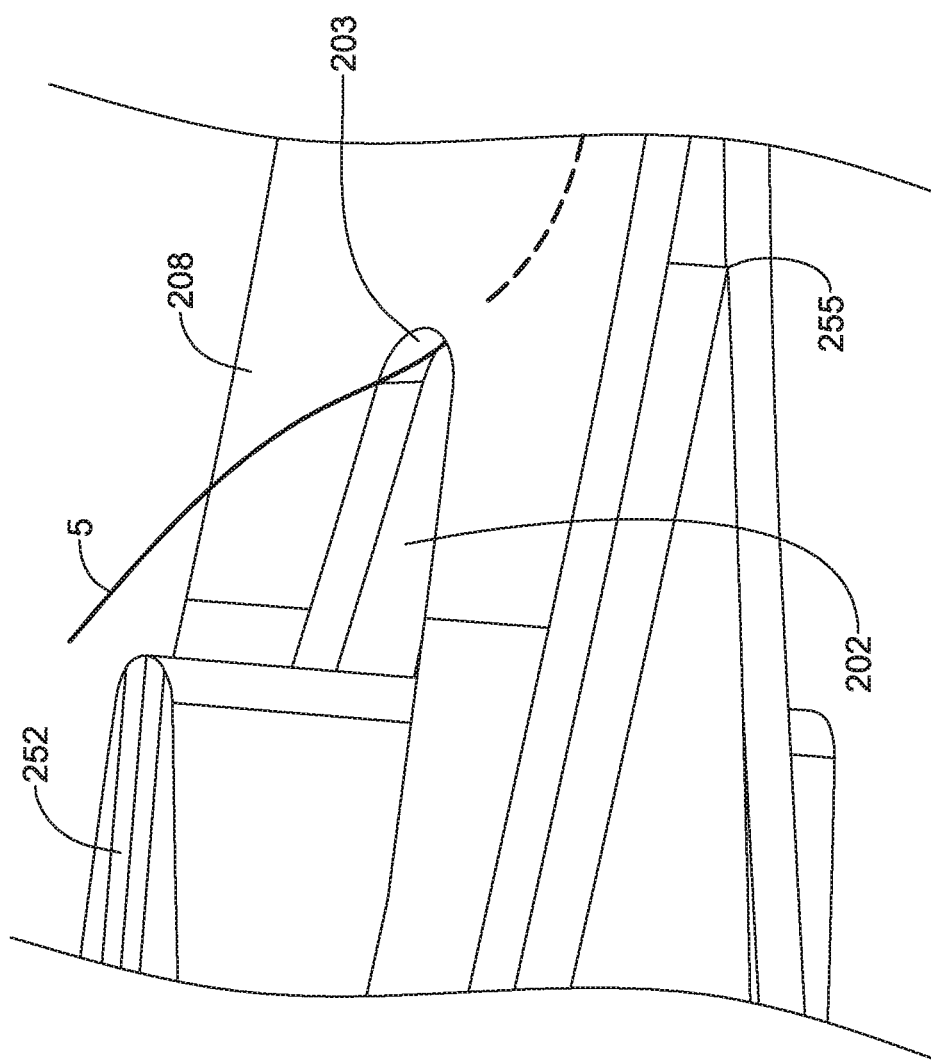

The cutter 250 is illustrated in FIG. 13. The sharp cutting edge 255 is the leading edge of the device and cuts the suture 5 as the suture 5 is clamped between the clamp arms 208. The cutter 250 may have opposing protrusions 252 configured to be received in enlarged key holes 202 in each clamp arm 208. See FIG. 14. The key holes 202 may be disposed between the spring section 205 and the proximal ends 218 of the clamp arms 208. The key holes 202 may be larger than the protrusions 252, allowing the suture 5 to be threaded through the key hole 202, as shown in FIGS. 15A and 15B. In some examples a cutting surface 203 may be provided on the distal end of the key hole 202 in one or both of the clamp arms 208, as shown in FIG. 15B. This cutting surface 203 may act in cooperation with the cutting edge 255 on the cuter 250 to cut the suture in a scissors like manner. In other examples, cutting surface 255 on the cutter 250 may not be a cutting surface but instead be a blunt edge configured to press the suture 5 against the cutting surface 203 on the key hole 202 to cut the suture as it is pressed between edge 255 and cutting surface 203. In FIG. 15A the suture 5 has been threaded through the key hole 202 with the clamp arms 208 partially clamped, and in FIG. 15B, the clamp arms 208 are in the fully closed and clamped position, and the suture 5 has been cut by the cutting edge 255 and/or the cutting surface 203.

Figure 16:
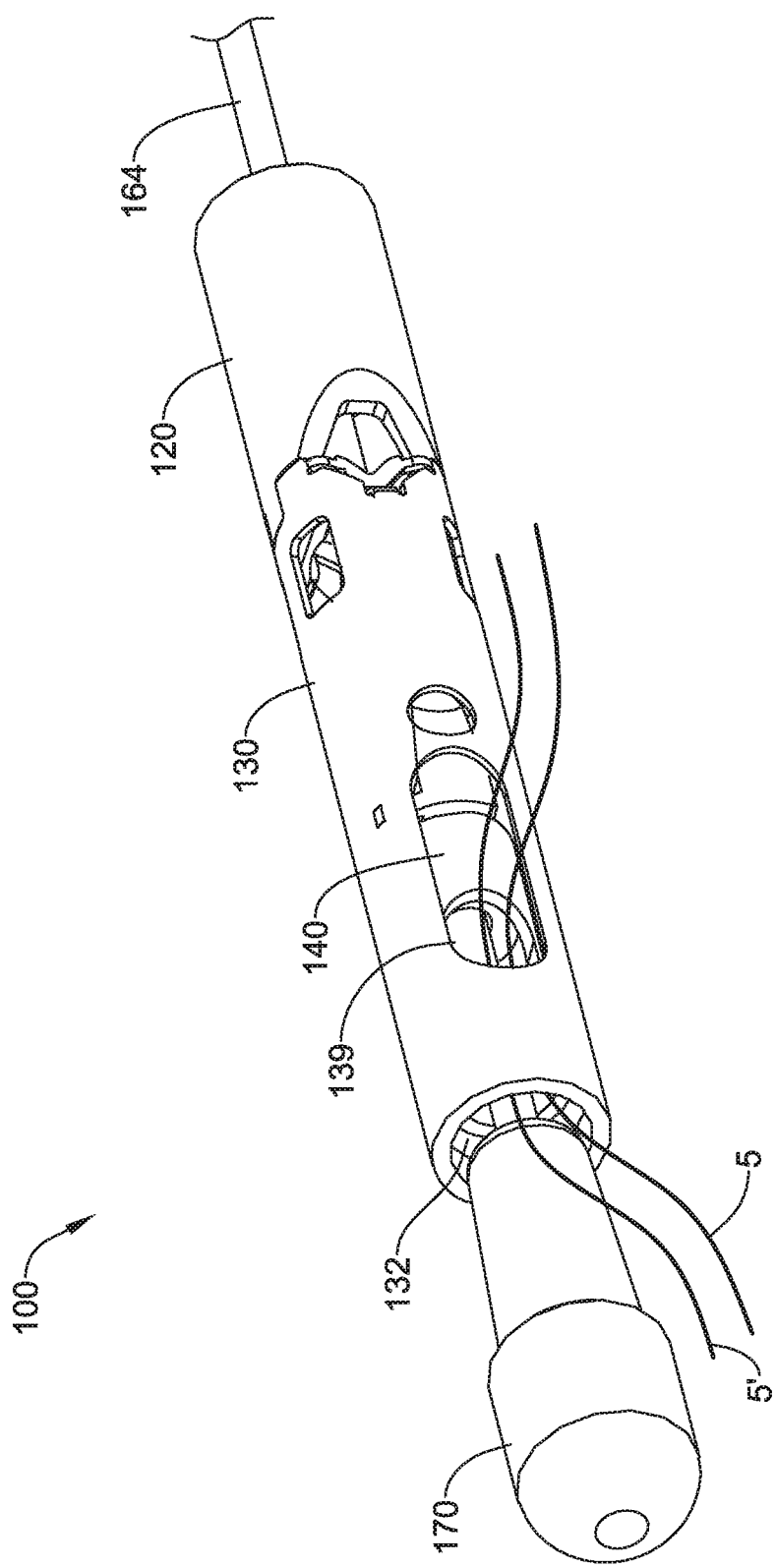
FIG. 16 is the medical device as shown in FIG. 1, with two sutures extending therethrough.

In the above discussion, the various example medical devices are described as being used to secure "a" suture and the figures illustrate a single suture 5 being secured and cut with the devices. It will be understood that any of the medical devices described herein may be used to secure and cut any number of sutures including one, two, three, four, five, etc. FIG. 16 illustrates the device 100 shown in FIG. 1, but here with two sutures 5, 5' threaded into the distal end 132 of the sleeve 130, through a portion of the cutter assembly 140, and out through a window 139 of the sleeve 130.

The materials that can be used for the various components of the medical devices disclosed herein may include those commonly associated with medical devices. Any of the devices, members and/or components of members or devices disclosed herein may be made from a metal, metal alloy, polymer (some examples of which are disclosed below), a metal-polymer composite, ceramics, combinations thereof, and the like, or other suitable material or composites of materials. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments polymers can be blended with a liquid crystal polymer (LCP). For example, the mixture can contain up to about 6 percent LCP.

Some examples of suitable metals and metal alloys include stainless steel, such as 304V, 304L, 316LV, and 17-7 stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A medical device for cinching and cutting one or more sutures, the medical device comprising:
   a coupler having a coupler lumen;
   a sleeve releasably coupled to the coupler, the sleeve having a sidewall defining a sleeve lumen, the sidewall having a window into the sleeve lumen;
   a cutter slidably disposed within the sleeve, the cutter having a cutting surface;
   a suture cinching member moveable into and out of the sleeve lumen; and
   a wire extending through and longitudinally movable within at least the coupler, the wire releasably connected to the cutter.

2. The medical device of claim 1, wherein when the wire is in a distal position, the suture cinching member is in a first configuration for receiving one or more sutures, and proximal movement of the wire pulls the suture cinching member at least partially into the sleeve into a second configuration in which a portion of the one or more sutures is cinched within the sleeve and cut by the cutting surface of the cutter.

3. The medical device of claim 2, wherein the cutter is configured such that when the suture cinching member is in the second configuration, further proximal movement of the wire causes the wire to be released from the cutter and the coupler to be released from the sleeve.

4. The medical device of claim 3, wherein the cutter comprises a cutting member and a cutter actuator, the cutting member defining a cutter lumen with an opening extending into the cutter lumen, the opening defining the cutting surface, wherein the cutter actuator includes a distal rod connected to the suture cinching member.

5. The medical device of claim 4, wherein the cutter actuator is connected to the suture cinching member and the wire, such that movement of the wire results in movement of the suture cinching member and the cutting member.

6. The medical device of claim 5, wherein the suture cinching member includes a proximal portion configured to fit within the sleeve lumen, wherein when the suture cinching member is in the first configuration, the suture cinching member is positioned such that the proximal portion is spaced apart from an inner surface of the sleeve and the cutter is positioned with the opening aligned with the window in the sleeve.

7. The medical device of claim 6, wherein when in the suture cinching member is moved to the second configuration, the suture cinching member and attached cutter are moved proximally until the proximal portion of the suture cinching member engages the inner surface of the sleeve and the opening in the cutter is proximal of the window in the sleeve.

8. The medical device of claim 3, wherein the suture cinching member has a distal head with an outer diameter greater than a diameter of the sleeve lumen, wherein in the second configuration the distal head abuts a distal end of the sleeve.

9. The medical device of claim 3, wherein the cutter is coupled to a yoke and the yoke is removably coupled to the wire, wherein the suture cinching member includes first and second opposing clamp arms fixed to the yoke.

10. The medical device of claim 9, wherein the yoke is axially moveable within the sleeve lumen between a first position in which distal ends of the first and second opposing clamp arms are spaced apart, and a second position in which the distal ends are in contact with one another.

11. The medical device of claim 10, wherein the first and second opposing clamp arms are biased in the first position such that when at least distal portions of the first and second opposing clamp arms are disposed distal of the sleeve, the first and second opposing clamp arms are in the first position, and moving the first and second opposing clamp arms proximally into the sleeve moves the first and second opposing clamp arms into the second position.

12. The medical device of claim 11, wherein the cutter is disposed between the first and second opposing clamp arms.

13. The medical device of claim 12, wherein the cutting surface is a linear cutting surface disposed transverse to a longitudinal axis of the sleeve.

14. The medical device of claim 13, wherein a distal end of the first clamp arm has a rounded concave surface and a distal end of the second clamp arm has a rounded convex surface configured to engage the rounded concave surface on the first clamp arm.

15. The medical device of claim 14, wherein when the first and second opposing clamp arms are in the second position, one or more sutures disposed between the first and second opposing clamp arms is clamped at a first location between the distal ends of the first and second opposing clamp arms and at a second location distal of the cutter.

16. The medical device of claim 15, wherein the cutter is configured such that when the first and second opposing clamp arms are moved from the first position to the second position over one or more sutures, the first and second opposing clamp arms clamp the one or more sutures and the cutting surface cuts the one or more sutures.

17. The medical device of claim 2, wherein the coupler has a projection extending into the coupler lumen, the cutter includes a proximal coupling member, and the wire includes a distal end removably coupled to the proximal coupling member of the cutter, wherein when the suture cinching member is in the second configuration, further proximal movement of the wire causes the proximal coupling member to engage the projection, stopping its proximal movement and releasing the distal end of the wire, and releasing the coupler from the sleeve.

18. The medical device of claim 2, wherein the sleeve has an opening through the sidewall proximal of the window, and the cutter further comprises at least one deflectable wing configured to move into the opening when the suture cinching member moves into the second configuration.

19. A medical device for applying a cinch to one or more sutures, the medical device comprising:
  an elongate shaft defining a shaft lumen;
  a sleeve having a sleeve lumen and a window extending into the sleeve lumen;
  first and second opposing clamp arms fixed to a yoke, wherein the yoke is axially moveable within the sleeve lumen between a first position in which distal ends of the first and second opposing clamp arms are spaced apart, and a second position in which the distal ends are in contact with one another;
  a cutter coupled to the first and second opposing clamp arms, the cutter defining a cutting surface, the cutter configured such that when the first and second opposing clamp arms are moved from the first position to the second position over one or more sutures, the first and second opposing clamp arms clamp the one or more sutures and the cutting surface cuts the one or more sutures.

20. A method of cinching and cutting one or more sutures, the method comprising:
  engaging one or more sutures with a suture cinching member, a distal portion of the suture cinching member disposed distal of a sleeve and a proximal portion of the suture cinching member disposed within a lumen of the sleeve, the suture cinching member connected to a cutter slidably disposed within the sleeve lumen; and
  moving the suture cinching member and connected cutter proximally into the sleeve, thereby engaging a cutting surface on the cutter with the one or more sutures and cutting the one or more sutures.

* * * * *